United States Patent [19]
Orenga et al.

[11] Patent Number: 5,599,293
[45] Date of Patent: Feb. 4, 1997

[54] ENVIRONMENTALLY FRIENDLY CATAMENIAL TAMPON ASSEMBLY AND METHOD OF CONSTRUCTION

[75] Inventors: John Orenga, Channahon, Ill.; Edwin H. Sailer, Ringoes, N.J.

[73] Assignee: McNeil-PPC, Inc., Skillman, N.J.

[21] Appl. No.: 429,980

[22] Filed: Apr. 27, 1995

Related U.S. Application Data

[63] Continuation of Ser. No. 998,484, Dec. 31, 1992, abandoned.

[51] Int. Cl.⁶ .................................................. A61F 13/20
[52] U.S. Cl. .................. 604/16; 604/18; 604/11
[58] Field of Search ..................... 604/11–18, 904

[56] References Cited

U.S. PATENT DOCUMENTS

| | | | |
|---|---|---|---|
| 4,891,042 | 1/1990 | Melvin et al. .................... | 604/11 |
| 5,153,971 | 10/1992 | Van Iten ............................ | 604/904 |

FOREIGN PATENT DOCUMENTS

| | | | |
|---|---|---|---|
| 392281 | 10/1990 | European Pat. Off. ............. | 604/11 |
| 2220359 | 1/1990 | United Kingdom ................ | 604/11 |
| 2013508 | 8/1992 | WIPO ................................. | 604/15 |

Primary Examiner—John G. Weiss
Assistant Examiner—Mark O. Polluta

[57] ABSTRACT

An environmentally-friendly-tampon assembly of the type which includes an inner sleeve, an outer sleeve and an absorbent pledget has inner and outer sleeves which are fabricated from a biodegradable, flushable material such as paper. The outer sleeve has an inwardly extending tang for preventing movement of the pledget during retraction of the inner sleeve. The tang is also formed of biodegradable material, and may be formed of material which is from the same blank out of which the outer sleeve was formed. Six different methods of forming the outer sleeve and tang are disclosed.

9 Claims, 6 Drawing Sheets

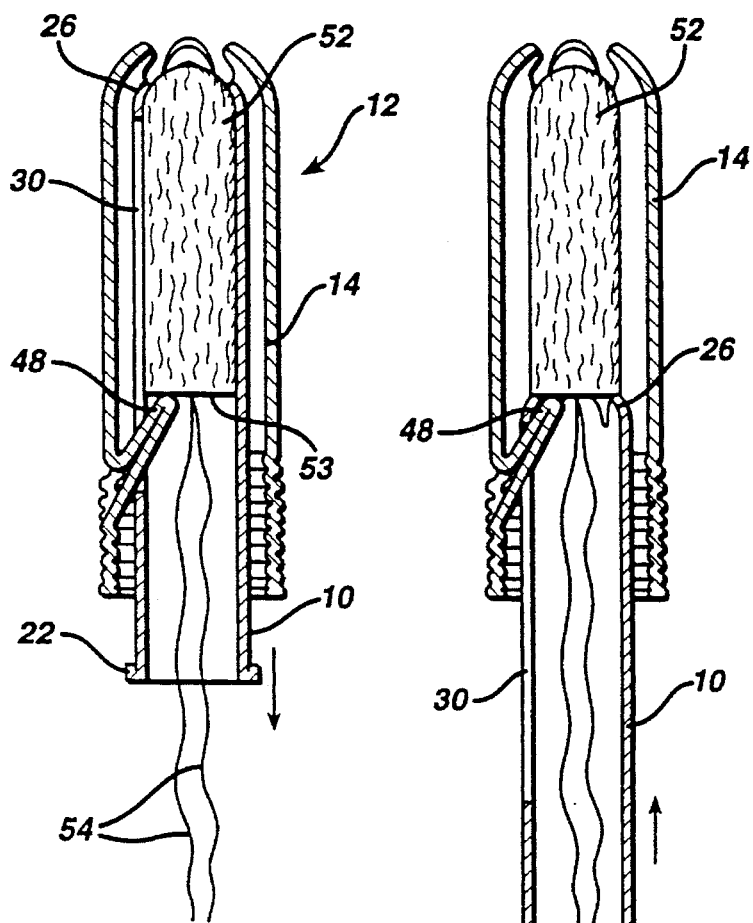
FIG. 3A
FIG. 3B
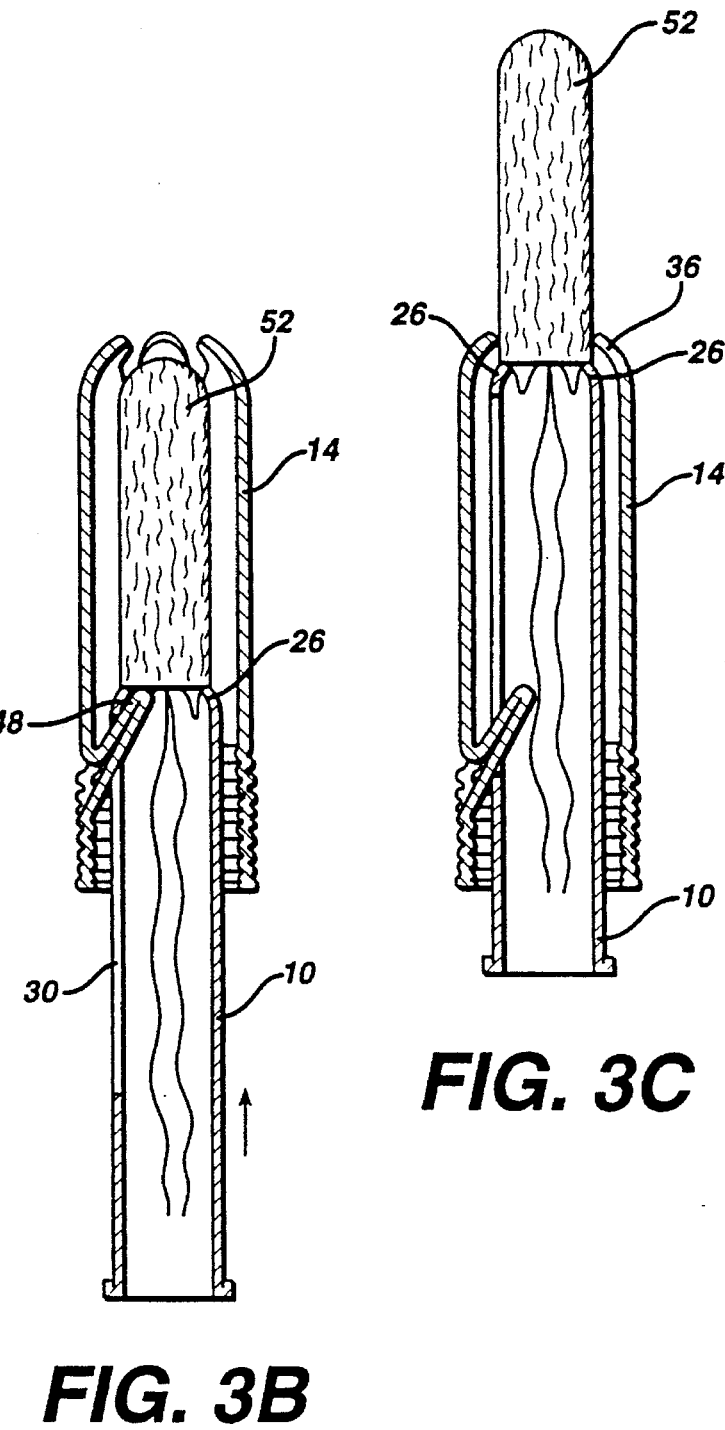
FIG. 3C

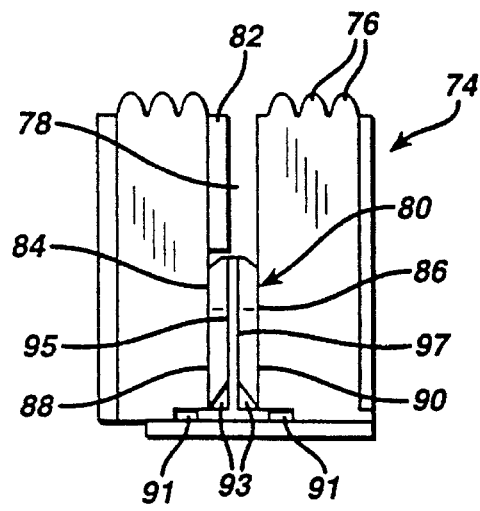
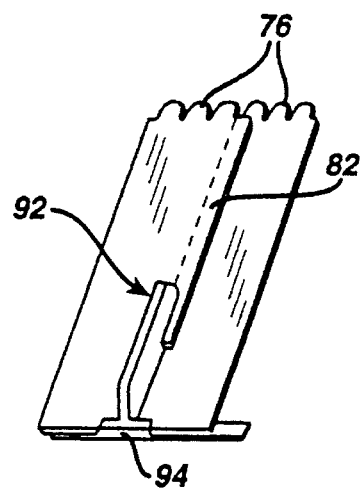
FIG. 5A  FIG. 5B
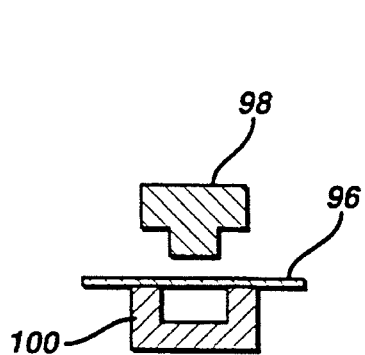
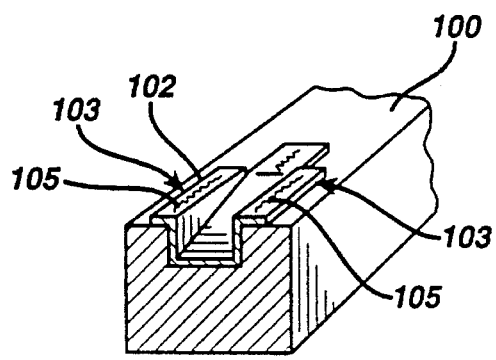
FIG. 6A  FIG. 6B
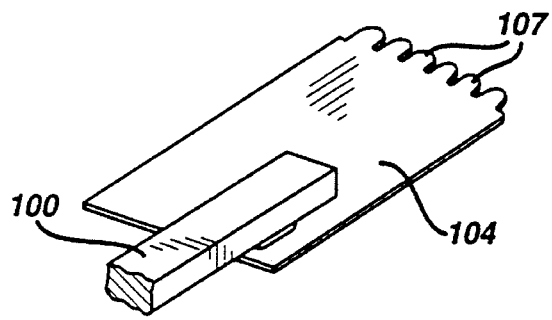
FIG. 6C

ENVIRONMENTALLY FRIENDLY CATAMENIAL TAMPON ASSEMBLY AND METHOD OF CONSTRUCTION

This is a continuation of application Ser. No. 07/998,484, filed Dec. 31, 1992, abandoned which is hereby incorporated by reference.

BACKGROUND OF THE INVENTION

1. Field of the Invention

This invention relates to the field of tampon applicators for positioning catamenial tampons. More specifically, this invention relates to an improved environmentally-friendly tampon applicator which is collapsible, biodegradable and flushable.

2. Description of the Prior Art

In the past, catamenial tampons have been applied and used either with or without applicators. Digital tampons are inserted into the vaginal cavity manually. Applicators, however, have been used in order to facilitate the insertion of the tampon and for the purposes of comfort and discretion. Generally, tampon applicators are composed of two separate concentric plastic or cardboard tubes which are in telescopic relationship to one another. The tube having a larger diameter cross-section is termed the outer sleeve, which generally retains the tampon plug, or pledget. The tube having a smaller diameter is termed the inner sleeve and is usually positioned within the outer sleeve behind the pledget. The inner sleeve is used to expel the pledget from the applicator during use.

For reasons relating to convenience and discretion, it is desirable that the tampon applicator be as small as possible. To that end, applicator designs have been introduced which provide for the inner and outer sleeves to be nested prior to use. Such designs are disclosed in U.S. Pat. Nos. 4,286,595 and 4,479,791. In such designs, the pledget is held in place with respect to the outer sleeve by a retaining element or tang when the inner sleeve is retracted. The inner sleeve is designed to engage a rear portion of the pledget once it has been retracted. After the inner sleeve has been retracted, then, the tampon may be expelled from the outer sleeve into the vaginal cavity by pushing with the inner sleeve.

The above-discussed tampon applicator designs have proved themselves to be effective and convenient. However, such applicators commonly are fabricated in part or in whole from plastics, which are not biodegradable or flushable.

It is clear that there has existed a long and unfilled need in the prior art for a tampon applicator which is collapsible, biodegradable and flushable.

SUMMARY OF THE INVENTION

Accordingly, it is an object of the invention to provide an improved catamenial tampon applicator which is fabricated from biodegradable material.

It is further an object of the invention to create a catamenial tampon applicator which is collapsible after use.

It is yet further an object of the invention to provide an improved catamenial tampon applicator which is fabricated from material which is safely flushable.

In order to achieve the above and other objects of the invention, a method of making an improved biodegradable inner sleeve for a tampon applicator, includes, according to one aspect of the invention, steps of (a) providing a tube which is fabricated from a biodegradable material; and (b) forming closure petals at one end of said tube, said closure petals being flexible and being bent at a distal end thereof toward a central axis of the tube, whereby a biodegradable inner sleeve for holding a absorbent pledget assembly is formed.

According to a second aspect of the invention, an inner sleeve for a tampon assembly of the type which includes an outer sleeve and a pledget of absorbent material includes a tube portion which is fabricated from a biodegradable material; and a plurality of petals at a first end of said tube portion, said petals being flexible and being bent at a distal end thereof toward a central axis of said tube, whereby a biodegradable inner sleeve for a tampon assembly is provided.

According to a third aspect of the invention, a method of making an outer sleeve for a tampon assembly, includes, in no essential order steps of (a) providing a tube blank of biodegradable material; (b) forming a retaining tang out of material in the tube blank; and (c) fabricating a tube from said tube blank so that the retaining tang is positioned adjacent to an inner surface of the tube, whereby the retaining tang can prevent movement of an absorbent pledget during use of the tampon assembly.

According to a fourth aspect of the invention, a method of making an outer sleeve for a tampon assembly includes, in no essential order, steps of (a) providing a tube blank of biodegradable material; (b) securing a retaining tang which is also fabricated from biodegradable material to the tube blank; and (c) fabricating a tube from the tube blank so that the retaining tang is positioned adjacent to an inner surface of said tube, whereby said retaining tang can prevent movement of an absorbent pledget during use of the tampon assembly.

According to a fifth aspect of the invention, an outer sleeve for a tampon assembly includes a tube which is fabricated from biodegradable material, said tube having an inner surface; and a retaining tang positioned adjacent the inner surface, the retaining tang also being fabricated from biodegradable material.

According to a sixth aspect of the invention, an environmentally friendly tampon assembly includes a pledget of absorbent material; an inner sleeve for containing the pledget, the inner sleeve being fabricated from a biodegradable material and having pushing structure at a forward end thereof for pushing the pledget; and an outer sleeve for slidably containing the inner sleeve, the outer sleeve also being fabricated from biodegradable material, the outer sleeve having a tang positioned adjacent to an inner surface thereof, the tang being constructed and arranged to hold the pledget in place when the inner sleeve is retracted with respect to the outer sleeve to engage the pushing means with the pledget, whereby the pledget can be conveniently inserted as a catamenial tampon.

These and various other advantages and features of novelty which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

FIGS. 3A–3C depict operation of the tampon assembly utilizing the inner and outer sleeves depicted in FIGS. 1A–1C and 2A–2E, respectively;

FIGS. 5A–5B depict fabrication of an outer sleeve for a tampon applicator according to a third, preferred embodiment of the invention;

FIGS. 6A–6C depict fabrication of an outer sleeve for a tampon applicator according to a fourth preferred embodiment of the invention;

DETAILED DESCRIPTION OF THE PREFERRED EMBODIMENT(S)

Figure 1A:
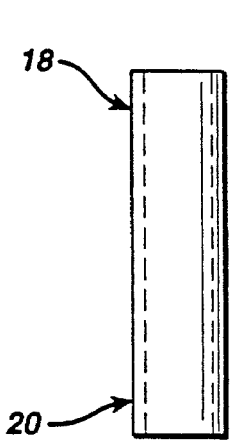
FIGS. 1A–1C depict the fabrication of an inner sleeve for an improved tampon applicator according to a preferred embodiment of the invention.

Referring now to the drawings, wherein like reference numerals designate corresponding structure throughout the views, and referring in particular to FIGS. 1A–1C, 2A–2E and 3A–3C, an improved collapsible, biodegradable and flushable tampon assembly 12 includes an inner sleeve 10, an outer sleeve 14 and a pledget assembly including an absorbent pledget 52 and a string 54, as may thus be seen in FIGS. 3A–3C.

Preferably, both inner sleeve 10 and outer sleeve 14 are fabricated from a biodegradable, flushable material, preferably paper. Most preferably, a multilayered paper material, either virgin or recycled, is used in conjunction with a water-based adhesive. The outer layer of material is most preferably coated with a smooth biodegradable material to enhance insertion comfort. Such coating materials may be polyvinyl alcohol, PHBV such as is available under the Biopol brand from ICI, Ltd., starch such as is available under the Novon brand from Warner-Lambert, destructured starch as is available from Novamont under the brand name Mater Bi, polyethylene glycol, or a natural coating such as beeswax.

Figure 1B:
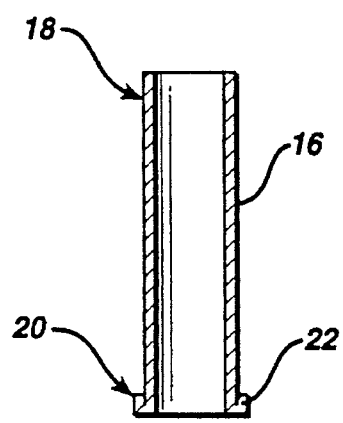
Figure 1C:
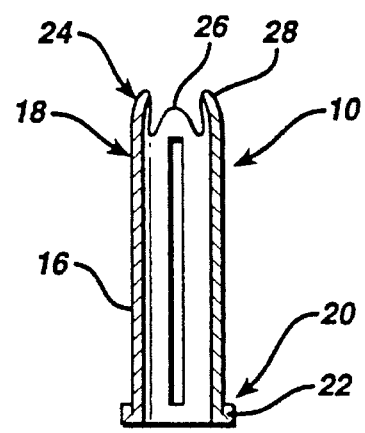

Referring now to FIG. 1C, inner sleeve 10 is formed from a tube 16 having a first end 18 and a second end 20. A ring 22 is formed on the second end 20 of tube 16 to provide a gripping surface for a user, as will be described in greater detail below. A plurality of petals 24 are defined on the first end 18 of tube 16. Petals 24 are bent inwardly toward a central axis of tube 18, as may best be seen in FIGS. 1C and 3A. The petals 24 include a number of longer petals 28, and at least one shorter petal 26, as is shown in FIG. 1C. The purpose of shorter petal 26 and longer petals 28 will be described in greater detail below.

FIGS. 1A–1C depict a method of forming an inner sleeve 10 according to a preferred embodiment of the invention. Referring first to FIG. 1A, a cylindrical tube 16 which is fabricated from a biodegradable, flushable material is first provided. Tube 16 has a first end 18 and a second end 20, as shown in FIG. 1A. As may be seen in FIG. 1B, gripping ring 22 is formed by rolling up a portion of the second end 20 of tube 16 and compressing the rolled up portion. Referring now to FIG. 1C, the petals 24 are then die-cut into the first end 18 of tube 16 so as to form the shorter petal 26 and the longer petals 28. A longitudinal slot is then cut into a side wall of tube 16. The edges 30 which define the longitudinal slot are illustrated in FIG. 1C. The purpose of longitudinal slot 30 will be described below in the description of operation of tampon assembly which is provided in relation to FIGS. 3A–3C.

Figure 2A:
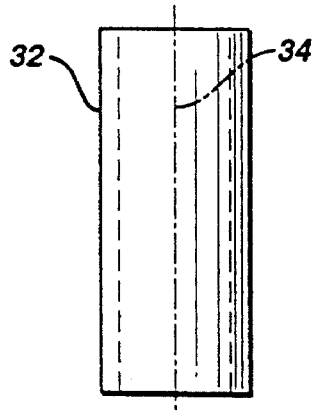
FIGS. 2A–2E depict fabrication of an outer sleeve for the tampon assembly according to a first, preferred embodiment of the invention.
Figure 2B:
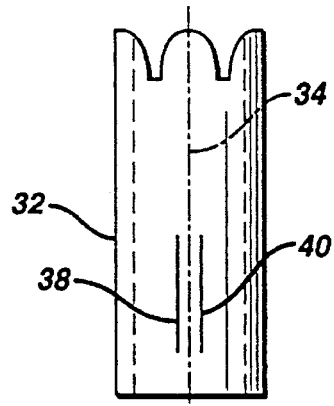
Figure 2C:
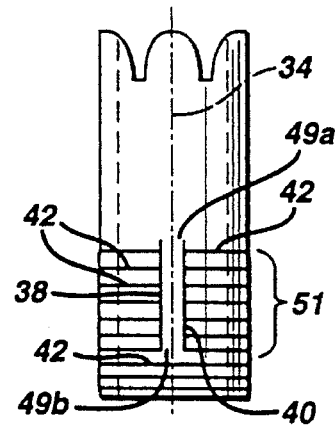
Figure 2D:
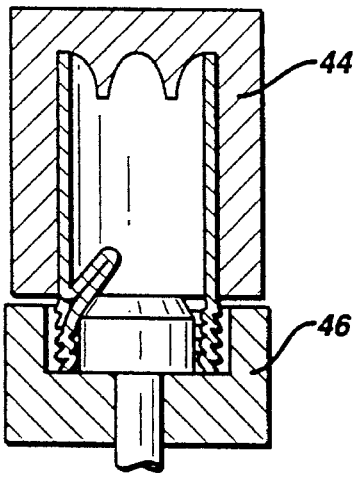
Figure 2E:
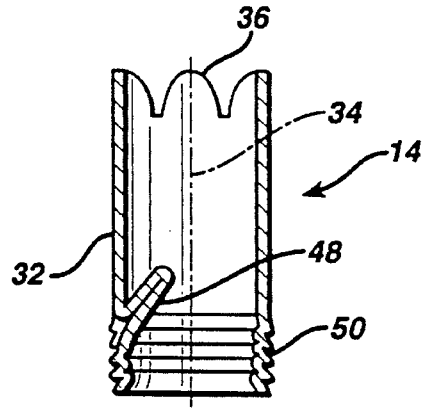

Referring briefly to FIG. 2E, a preferred embodiment of outer sleeve 14 includes a tube 32 which is formed from a biodegradable, flushable material. Outer sleeve 14 further includes a plurality of petals 36 defined in a first, upper end of tube 32, and a handle portion 50 defined in a second, lower portion of tube 32. Outer sleeve 14 further includes an inwardly extending tang 48 which is formed from a tang-forming portion of the outer sleeve tube 32. The tang 48 projects inwardly from first and second tang ends 49a, 49b at tube 32 toward a center axis 34 of tube 32.

A preferred method for forming the outer sleeve 14 is illustrated in FIGS. 2A–2E. As may be seen in FIG. 2A, a tube 32 of biodegradable, flushable material is provided which has a center axis 34. As may be seen in FIG. 2B, petals 36 are first die-cut into a first, upper end of tube 32. At about the same time, first and second longitudinal slits 38, 40 are made in an outer wall of tube 32. Slits 38, 40 are made through the entire thickness of the outer wall of tube 32, and are preferably parallel to each other and to the center axis 34 of tube 32. After first and second slits 38,40 have been made, a plurality of circumferential scores 42 are made in the outer wall of tube 32 at regular spaced intervals from the top of slits 38, 40 to the second lower end of tube 32. Circumferential scores 42 do not extend through the entire thickness of outer wall of tube 32, but are made in order to facilitate folding of the material from which tube 32 is made at the location of the scores 42. Circumferential scores 40 further do not extend in the area between slits 38,40. Referring now to FIG. 2D, the tube 32 depicted in FIG. 2C is placed in a forming die assembly including a stationery support die 44 and a moving crimp die 46. As is shown in FIG. 2D, lower crimp die 46 is moved toward stationary die 44 for a predetermined distance, which causes the outer wall of tube 32 to collapse along the circumferential score lines 44. Simultaneously, the area defined between first and second slits 38, 40 folds inwardly along a crease which coincides with the score line formed therein to form the inwardly extending tang 48 shown in FIG. 2E. As may be seen in FIG. 2E, the collapsed lower portion of the tube 32 forms the handle portion 50, which is densified and smoothed to become a rigid finger grip zone. The collapsing of at least a portion 51 of the lower portions brings the first and second tang ends 49a, 49b, together and allows the center portion of the tang to extend into the interior of the sleeve.

Referring now to FIGS. 3A–3C, it will be seen that tampon assembly 12 is formed by inserting the absorbent pledget 52 into the inner sleeve 10 from the second end 20 to the first end 18 of inner sleeve 10. Pledget 52 is thus nested within and partially enclosed by the petals 24 at the first end 18 of inner sleeve 10. Inner sleeve 10 and pledget 52 are then inserted into the outer sleeve 14 in such a manner that the tang 48 of outer sleeve 14 extend through the slot 30 that is defined in the outer wall of the tube 16 of inner sleeve 10. After such assembly, tang 48 is positioned beneath pledget 52 so as to engage a bottom surface 53 of pledget 52.

In order to use tampon assembly 12, a consumer first grips the second lower end 20 of inner sleeve 10 by gripping ring 22 and retracts inner sleeve 10 from outer sleeve 14 in the manner that is depicted in FIG. 3B. As this occurs, pledget 52 will be retained in place relative to outer sleeve 14 by the force exerted by tang 48 against the bottom surface 53 of pledget 52. As inner sleeve 10 is retracted, petals 24 will be spread outwardly by pledget 52 and will be drawn downwardly around pledget 52 until reaching the bottom surface 53 of pledget 52. At this point, depicted in FIG. 3B, the shorter petal 26 will spring inwardly again to a position which is beneath the bottom surface 53 of pledget 52. At this point of retraction, the consumer will then begin to reinsert inner sleeve 10 into outer sleeve 14. The pressure which is exerted by shorter petal 26 against the bottom surface 53 of pledget 52 will cause the pledget 52 to be forced upwardly by the motion of inner sleeve 10 as it is reinserted into outer sleeve 14. This will force the pledget 52 through the petals 36 of outer sleeve 14 so that the pledget 52 may be safely and efficiently inserted into the vaginal cavity.

Figure 4A:
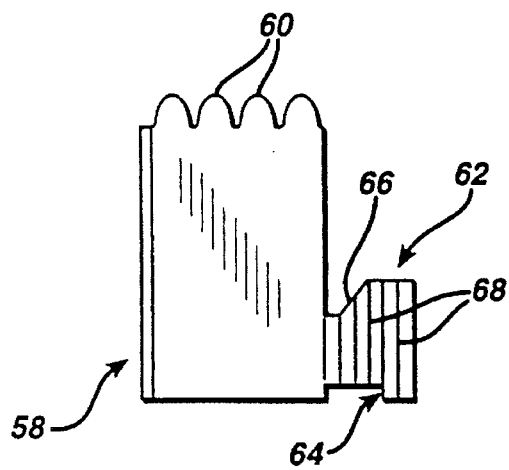
FIGS. 4A–4F depict formation of an outer sleeve according to a second, preferred embodiment of the invention.
Figure 4B:
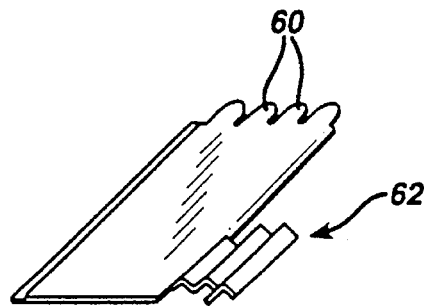
Figure 4C:
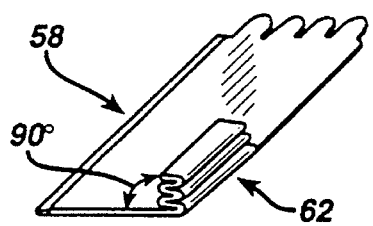
Figure 4D:
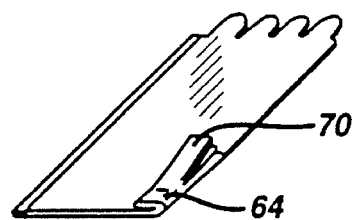
Figure 4E:
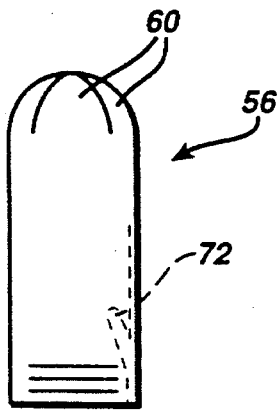
Figure 4F:
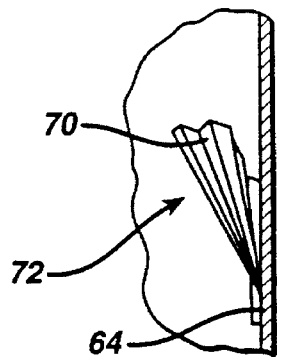

FIGS. 4A–4F depict a method for forming an outer sleeve 56 according to a second preferred embodiment of the invention. Referring first to FIG. 4A, a tube blank 58 is provided which includes a rectangular portion having a plurality of petals 60 formed on an upper end thereof, and a projection 62 extending outwardly from a lower end of the rectangular portion. Projection 62 is also substantially rectangular, although it has a recess 66 defined in an upper end thereof, and a square recess defined in a lower end thereof which defines an anchor tab 64. A plurality of vertical score lines 68 are defined at regularly spaced intervals on projection 62. Score lines 68 do not extend through the entire thickness of projection 62. Referring to FIG. 4B, projection 62 is first folded at the point of score lines 68 so as to create a series of alternating ridges in projection 62. Projection 62 is then folded upwardly so as to be substantially perpendicular to the remainder of tube blank 58, as shown in FIG. 4C. Anchor tab 64 is then affixed to remainder tube blank 58 by an adhesive, as is shown in FIG. 4D. After anchor tab 64 has been so secured, the rest of projection 62 remains as a portion 70 which fans out from the surface of tube blank 58, as may be seen in FIG. 4D. Tube blank 58 is then rolled so that the rectangular portion thereof is formed into a tube, as shown in FIG. 4E. At about the same time, petals 60 are pressed so as to bend inwardly toward the central axis of the so formed outer sleeve 56. The fanned-out portion 70 of projection 62 thus becomes an inwardly extending tang 72, as may be seen in FIGS. 4E and 4F.

Referring now to FIGS. 5A–5B, a tube blank 74 for forming an outer sleeve according to a third preferred embodiment of the invention, will now be described. As may be seen in FIG. 5A, tube blank 74 is substantially rectangular in shape and includes a plurality of petals 76 which are formed at a top end thereof. Tube blank 74 is cut at a central portion thereof so as to define a central space 78 and a tang forming portion 80. Tang forming portion 80 is defined by a pair of slits 84, 86 which extend through the entire thickness of tube blank 74, and a pair of scores 88, 90 which, respectively, are aligned and positioned beneath slits 84, 86. Cut out portions 91, 93 are provided at the lower end of tub blank 74 for purposes that will be apparent when viewing FIG. 5B. To form an outer sleeve from tube blank 74, tube blank 74 is folded along score lines 88, 90 so as to position a tab portion 82 defined on one side of space 78 over the edge which defines the opposite side of space 78. In the process, the tang forming portion 80 folds at scores 95, 97 so as to raise a square profiled tang 92 from the surface of tube blank 74. Simultaneously, the portion 99 of tang forming portion 80 which is between cut out portions 91 will form a surface 94 of tang 92 which is flush with the surface of the tube blank 74 after folding. Tube blank 74 may then be kept in its folded position through use of adhesives, and my then be folded into an outer sleeve.

Referring now to FIG. 6A–6C, a method for forming an outer sleeve according to a fourth embodiment of the invention utilizes a tang blank 96 which is positioned between first and second forming dies 98, 100. Dies 98, 100 are forced together in order to form a tang insert 102, as is best shown in FIG. 6B. Tang insert 102 includes a pair of flat surfaces 103 on which an adhesive 105 is placed. According to the preferred embodiment of the method, tang insert 102 is kept in second die 100 after the application of adhesive 105 to surfaces 103. Second die 100 is then moved relative a rectangular tube blank 104 having petals 107 defined therein. Second die 100 is then pressed against tube blank 104 to cause the tang insert 102 to become adhered to an inside surface of tube blank 104. Tube blank 104 is then rolled into a tube to complete the fabrication of an outer sleeve according to the fourth embodiment of the invention.

Figure 7A:
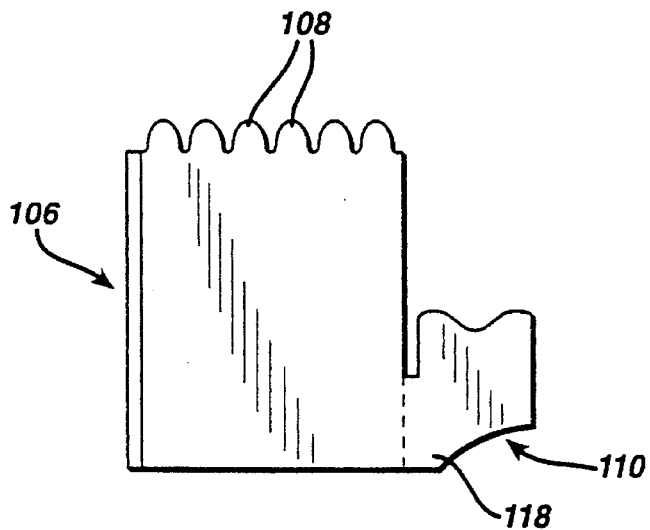
FIGS. 7A–7D depict fabrication of an outer sleeve for a tampon applicator according to a fifth preferred embodiment of the invention.
Figure 7B:
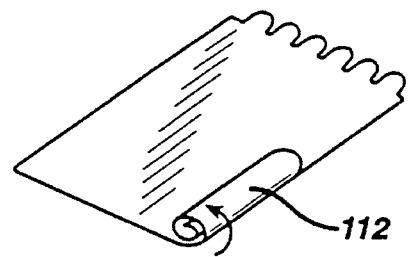
Figure 7C:
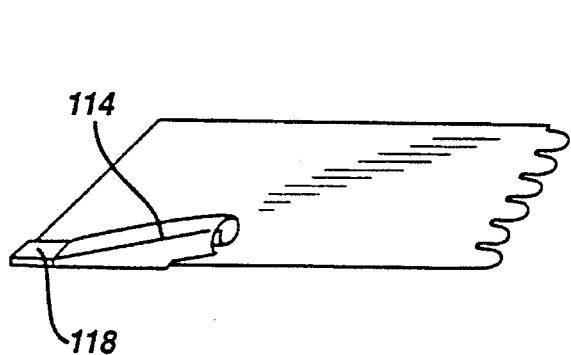
Figure 7D:
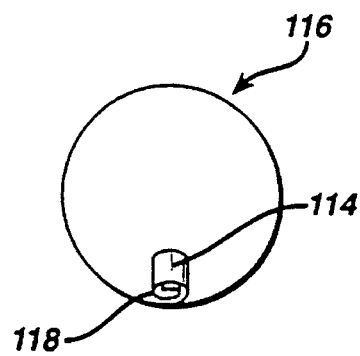

A method for fabricating an outer sleeve according to a fifth embodiment of the invention is depicted in 7A–7D. As may be seen in FIG. 7A, a tube blank 106 includes a plurality of petals 108 formed on a rectangular portion thereof, and a projection 110 which extends from a lower end of the rectangular portion. Projection 110 is shaped so as to define an anchor tab 118 on a lower end thereof. According to this embodiment of the invention, projection 110 is rolled up into a rolled projection 112, as may be seen in FIG. 7B. Anchor tab 118 is then adhered to the surface of tube blank 106, as may be seen in FIG. 7C. This process causes the remainder of rolled up projection 112 to project outwardly as a tang 114. Tube blank 106 is then formed into a tube to form an outer sleeve 116 according to the fifth embodiment of the invention, as shown in FIG. 7D.

Figure 8A:
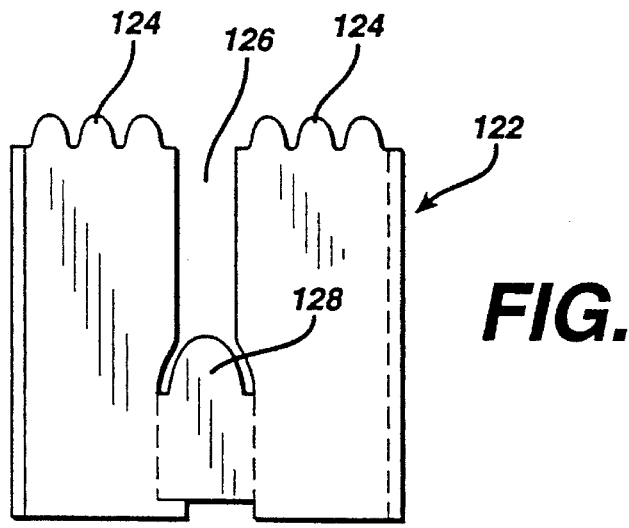
FIGS. 8A–8C depict fabrication of an outer sleeve for a tampon applicator according to a sixth preferred embodiment of the invention.
Figure 8B:
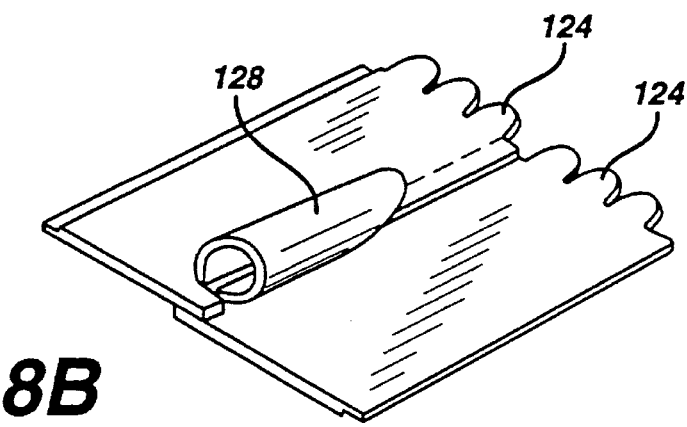
Figure 8C:
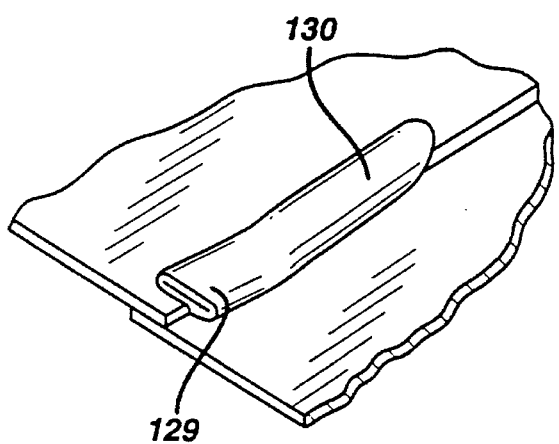

A method of forming a outer sleeve according to sixth embodiment of the invention is depicted in FIGS. 8A–8C. According to this embodiment of the invention, a tube blank 122 is substantially rectangular in shape, and includes a plurality of petals 124 on an upper end thereof. Tube blank 122 includes a space 126 defined in a central area thereof along with a tang forming portion 128. As may be seen FIG. 8B, the portions of tube blank 122 on each side of space 126 may be pulled together so as to form the tang forming portion of 128 into an internal roll or tube. After rolling, a roller portion 129 of tang forming portion 128 is secured to the tube blank 122 with an adhesive or other suitable means to form tang 130, as may best be seen in FIG. 8C. Tube blank 122 is then rolled into a tube to form an outer sleeve to form an outer sleeve according to the sixth embodiment of the invention.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. An environmentally friendly tampon assembly, comprising:

a pledget of absorbent material;

an inner sleeve for containing said pledget, said inner sleeve being fabricated from a biodegradable material and having pushing means at a forward end thereof for pushing said pledget; and a substantially tubular outer sleeve for slidably containing said inner sleeve, said outer sleeve comprising biodegradable material, said outer sleeve having a longitudinal direction and a tang comprising an inwardly-projecting folded tang-forming portion of said outer sleeve, said tang-forming portion having first and second ends made substantially adjacent by collapsing a portion of the outer sleeve in a longitudinal direction to form a finger grip.

2. A tampon assembly according to claim 1, wherein said inner and outer sleeves are both fabricated from a material which is both biodegradable and flushable.

3. A tampon assembly according to claim 1, wherein said inner and outer sleeves are both fabricated from a material comprising paper.

4. A tampon assembly according to claim 1, wherein said outer sleeve is folded along at least one fold line to form said retaining tang.

5. A tampon assembly according to claim 4, wherein said outer sleeve is prescored at said fold line.

6. A tampon assembly according to claim 1, wherein said outer sleeve has two slits formed therein, said tang being formed from material between said two slits.

7. A tampon assembly according to claim 6, wherein said outer sleeve is compressed in a direction in which said slits extend, and the material defined between the slits is folded to form said tang.

8. A tampon assembly according to claim 1, wherein said tube portion has a slot defined therein for receiving a projecting tang of an outer sleeve of the tampon assembly.

9. A tampon assembly according to claim 1, wherein said tube has a flange at a second end which is opposite said first end on which said petals are provided.

* * * * *